United States Patent
Shimase et al.

(10) Patent No.: US 10,208,277 B2
(45) Date of Patent: Feb. 19, 2019

(54) FLOW-PATH CONTROL METHOD, AND CELL CULTURE DEVICE

(71) Applicant: Hitachi High-Technologies Corporation, Tokyo (JP)

(72) Inventors: Akihiro Shimase, Tokyo (JP); Kazumichi Imai, Tokyo (JP); Eiichiro Takada, Tokyo (JP); Sadamitsu Aso, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 37 days.

(21) Appl. No.: 15/107,548

(22) PCT Filed: Dec. 24, 2014

(86) PCT No.: PCT/JP2014/084015
§ 371 (c)(1),
(2) Date: Jun. 23, 2016

(87) PCT Pub. No.: WO2015/111347
PCT Pub. Date: Jul. 30, 2015

(65) Prior Publication Data
US 2016/0319233 A1 Nov. 3, 2016

(30) Foreign Application Priority Data

Jan. 27, 2014 (JP) ................. 2014-012071

(51) Int. Cl.
*F16K 27/00* (2006.01)
*C12M 1/00* (2006.01)
(Continued)

(52) U.S. Cl.
CPC ....... *C12M 23/40* (2013.01); *B01L 3/502738* (2013.01); *B01L 3/567* (2013.01);
(Continued)

(58) Field of Classification Search
CPC .................................. C12M 23/40; F16K 7/06
(Continued)

(56) References Cited

U.S. PATENT DOCUMENTS

| 6,079,691 A * | 6/2000 | Dragone ............... F16K 7/06 251/4 |
| 2013/0143307 A1 | 6/2013 | Nozaki et al. |
| 2014/0087455 A1 | 3/2014 | Kobayashi et al. |

FOREIGN PATENT DOCUMENTS

| JP | 60-093356 A | 5/1985 |
| JP | 64-012265 A | 1/1989 |

(Continued)

OTHER PUBLICATIONS

International Search Report of PCT/JP2014/084015 dated Apr. 14, 2015.

*Primary Examiner* — Sean E Conley
*Assistant Examiner* — Holly M Mull
(74) *Attorney, Agent, or Firm* — Mattingly & Malur, PC

(57) ABSTRACT

According to the present invention, a problem of closed systems, namely minimizing the number of electromagnetic valves required to control a plurality of flow paths, can be addressed, and thus a low-cost cell culture device can be achieved. In this flow-path control method for X number of flow paths satisfying $X \leq 2^N$, the X number of flow paths are selected by using N number of valves to simultaneously and selectively control the opening and closing of the plurality of flow paths.

15 Claims, 7 Drawing Sheets

(51) Int. Cl.
*B01L 3/00* (2006.01)
*F16K 7/04* (2006.01)
*F16K 7/06* (2006.01)

(52) U.S. Cl.
CPC ............ *C12M 23/14* (2013.01); *C12M 23/58* (2013.01); *C12M 29/00* (2013.01); *F16K 7/045* (2013.01); *B01L 2200/025* (2013.01); *B01L 2200/0668* (2013.01); *B01L 2300/0816* (2013.01); *B01L 2300/0838* (2013.01); *B01L 2300/0861* (2013.01); *B01L 2400/0487* (2013.01); *B01L 2400/0622* (2013.01); *B01L 2400/0655* (2013.01)

(58) Field of Classification Search
USPC ...................................................... 435/289.1
See application file for complete search history.

(56) References Cited

FOREIGN PATENT DOCUMENTS

| | | |
|---|---|---|
| JP | 2008-054603 A | 3/2008 |
| JP | 2011-142837 A | 7/2011 |
| JP | 2012-217435 A | 11/2012 |
| WO | 2012/020458 A1 | 2/2012 |

\* cited by examiner

[FIG. 1]
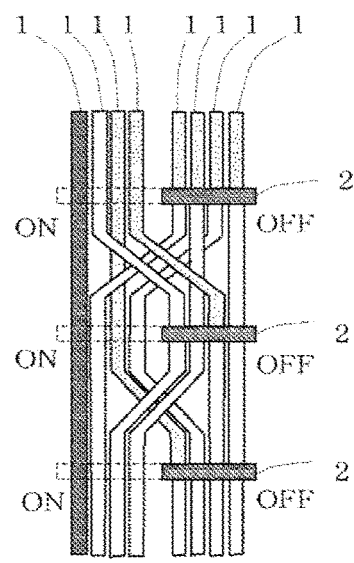
[FIG. 2]
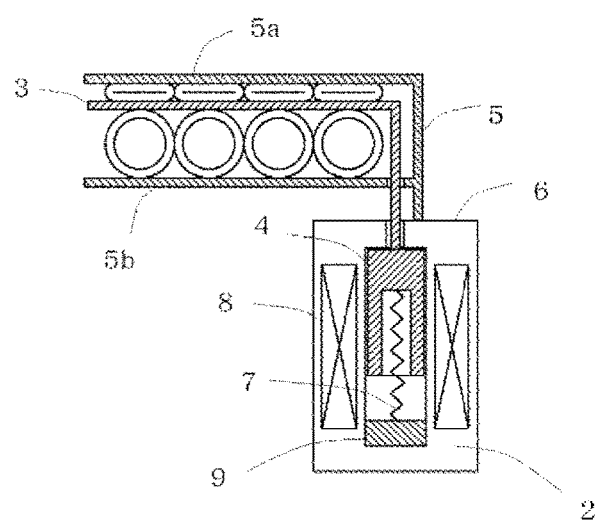

[FIG. 3]
(a)
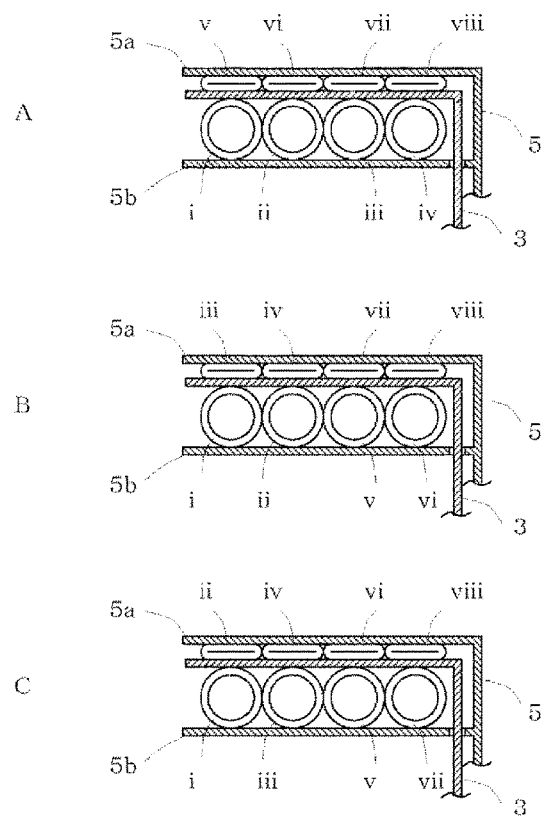
(b)
| TUBE # | A | B | C |
|---|---|---|---|
| i | NO | NO | NO |
| ii | NO | NO | NC |
| iii | NO | NC | NO |
| iv | NO | NC | NC |
| v | NC | NO | NO |
| vi | NC | NO | NC |
| vii | NC | NC | NO |
| viii | NC | NC | NC |

[FIG. 4]
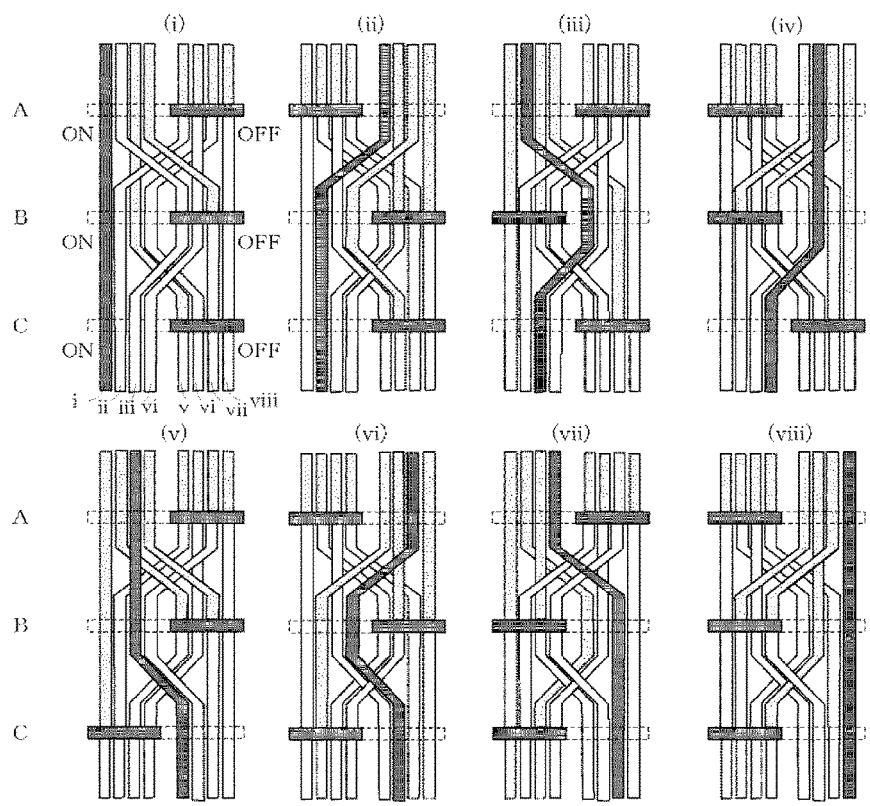

[FIG. 5]
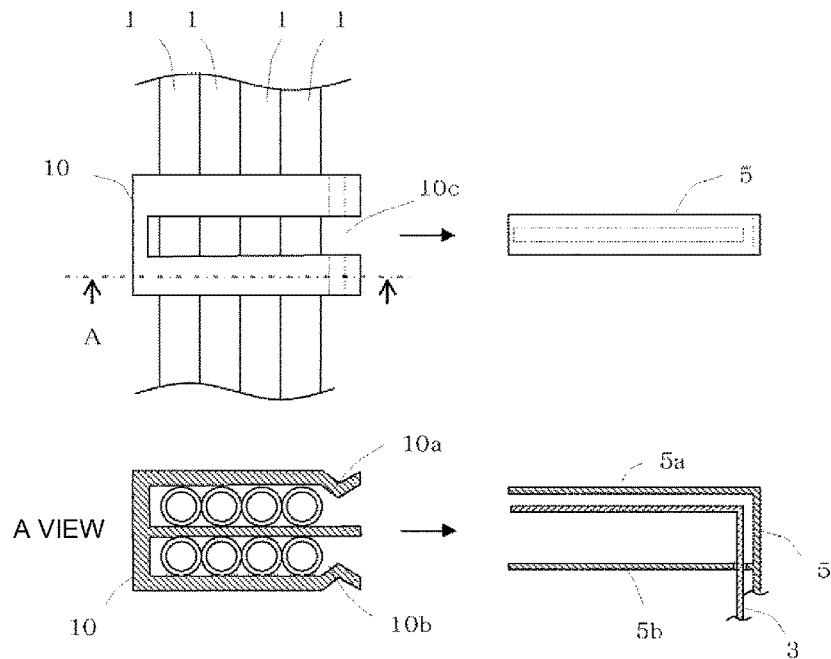
[FIG. 6]
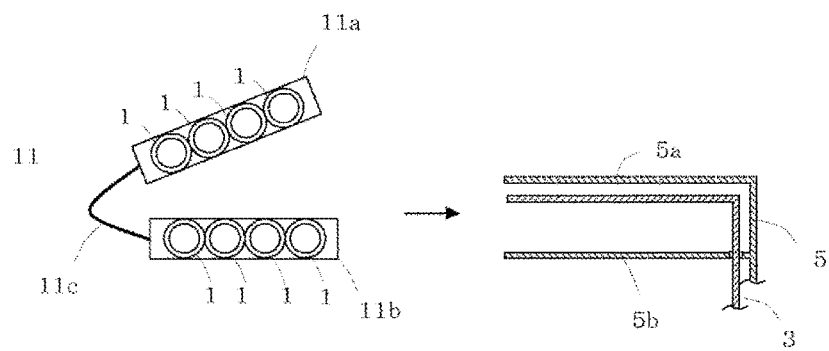

[FIG. 7]
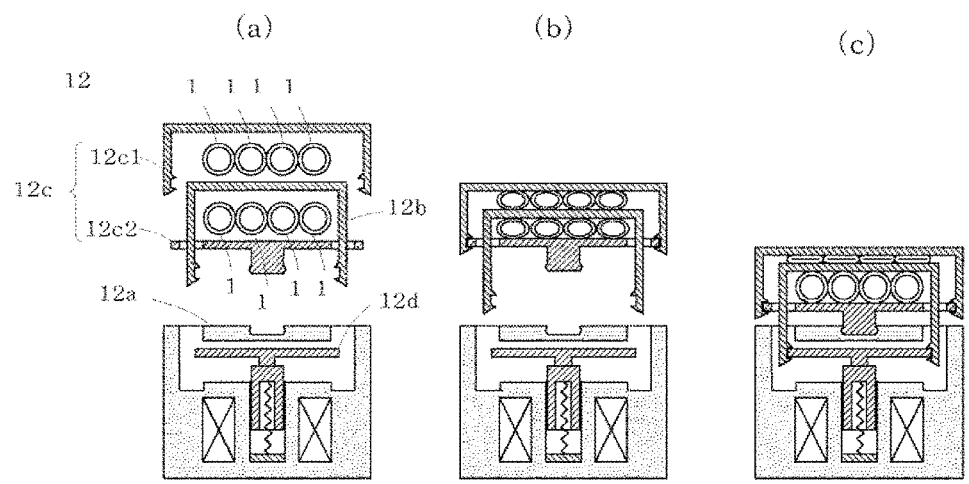
[FIG. 8]
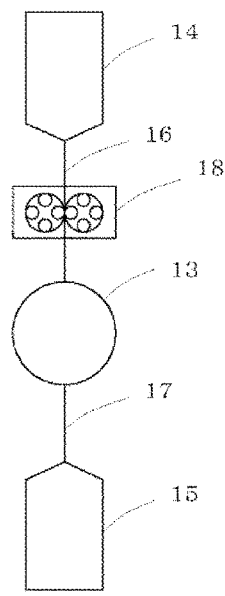

[FIG. 9]
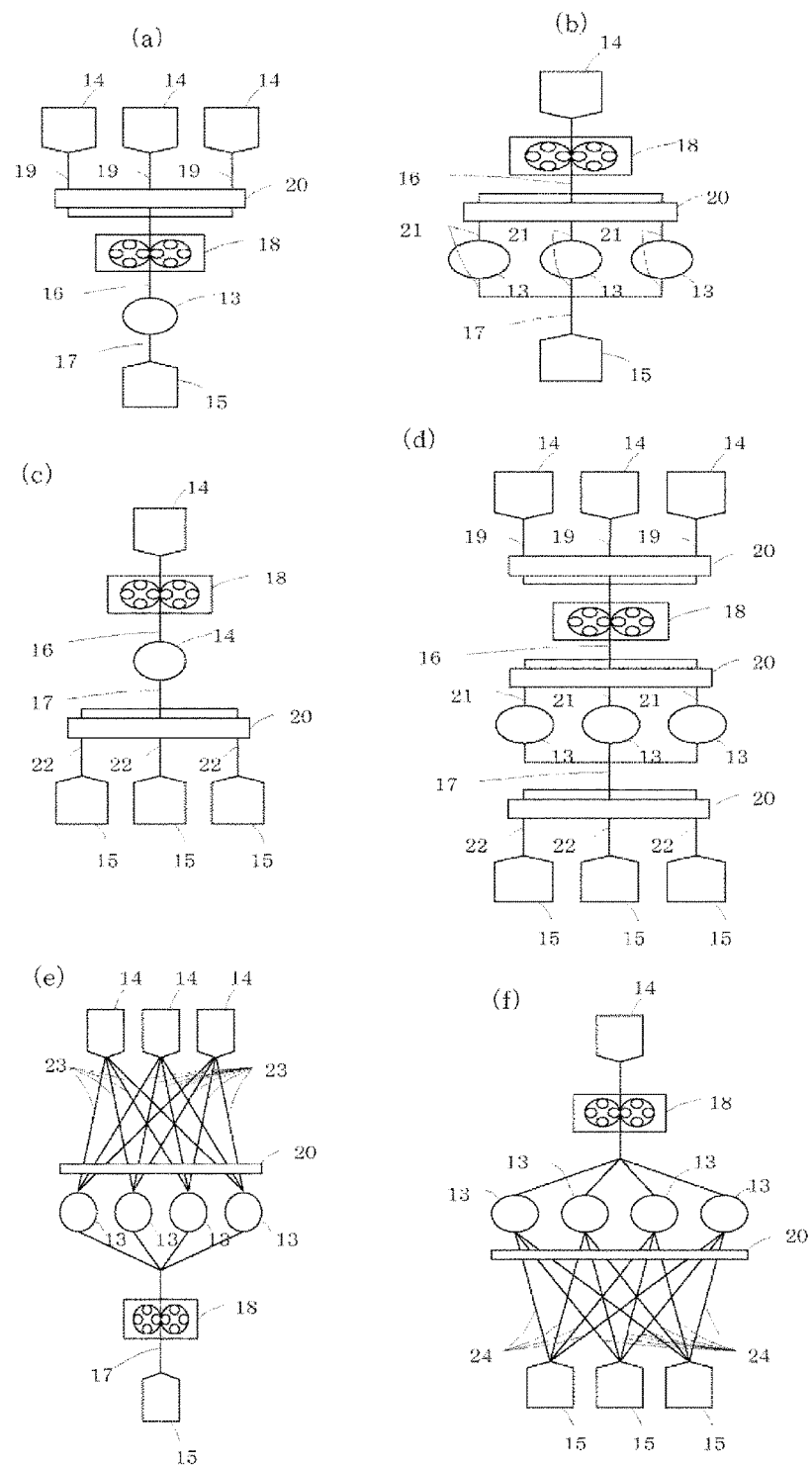

[FIG. 10]
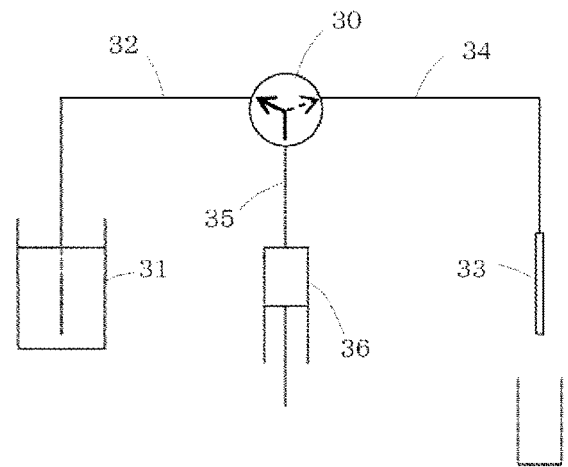
[FIG. 11]
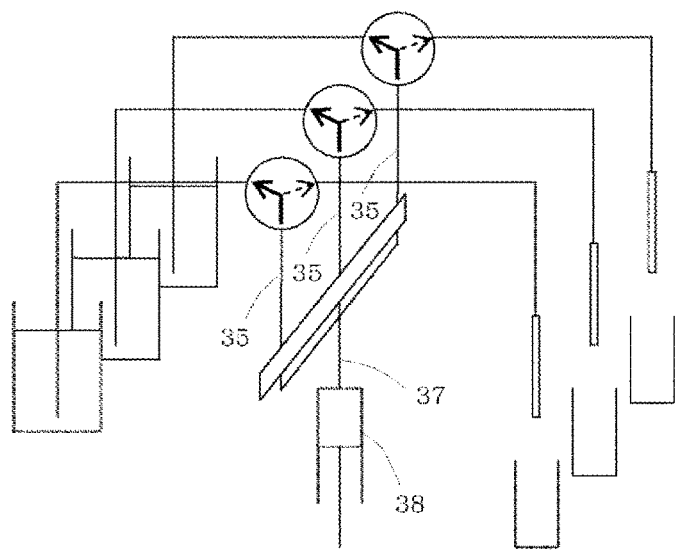

FLOW-PATH CONTROL METHOD, AND CELL CULTURE DEVICE

TECHNICAL FIELD

The present invention relates to a valve for flow-path control in a device including a plurality of flow paths such as a cell culture device or an automatic analysis device.

BACKGROUND ART

There is a valve called multiple switching valve for dispensing a plurality of reagents with one cylinder. An example of an automatic analysis device including the valve is described in JP-A-60-93356.

There is a valve called pinch valve for crushing (pinching) a flow path having elasticity from the outer side and controlling fluid. Examples of a cell culture device and an automatic analysis device including the valve are respectively described in JP-A-2011-142837 and JP-A-1-12265.

CITATION LIST

Patent Literature

Patent Literature 1: JP-A-60-93356
Patent Literature 2: JP-A-2011-142837
Patent Literature 3: JP-A-1-12265

SUMMARY OF INVENTION

Technical Problem

The pinch valve can control opening and closing of a flow path without directly touching fluid flowing on the inner side of the flow path. Therefore, it is unlikely that the fluid is contaminated. The valve itself is not soiled. Therefore, the pinch valve is appreciated in devices in which contamination is concerned such as a cell culture device and an automatic analysis device. In particular, in the cell culture device, basically, a flow path contaminated by a flow of a culture medium or the like is discarded. The pinch valve not soiled in itself can be economically recycled.

When there are a plurality of flow paths and it is attempted to selectively control opening and closing, if pinch valves are provided in the respective flow paths, at least the control is possible. However, if the number of flow paths increases, the number of pinch valves also increases. This leads to an increase in costs and the device is increased in size.

For the control of the plurality of flow paths, it is also conceivable to use the multiple switching valve described in Patent Literature 1. However, since the inside of the valve is in contact with liquid, use of the multiple switching valve is undesirable from the viewpoint of contamination.

There is a demand for a valve that has less risk of contamination and is small in size and inexpensive.

Solution to Problem

In order to solve the problems, for example, a configuration described in claims is adopted.

This application is a flow-path control method for X number of flow paths satisfying $X \leq 2^N$. The X number of flow paths are selected by selectively simultaneously controlling opening and closing of the plurality of flow paths using N number of valves.

Advantageous Effect of Invention

According to the present invention, it is possible to eliminate a risk of contamination and minimize the number of pinch valves required for control of a plurality of flow paths. Therefore, it is possible to reduce the size and the costs of a device.

BRIEF DESCRIPTION OF THE DRAWINGS

FIG. 1 is a schematic explanatory diagram of a flow-path control method of the present invention.
FIG. 2 is a diagram showing the structure of a universal-type pinch valve.
FIG. 3 is a diagram showing a method of inserting eight tubes through pinch valves in three places.
FIG. 4 is a diagram showing a pinch-valve control method for tube selection.
FIG. 5 is a diagram showing an example in which tubes to be on an NC side and tubes to be on an NO side in the pinch valves are sorted and collected and can be collectively set.
FIG. 6 is a diagram showing another example of a tube holder.
FIG. 7 is a diagram showing an example of the structures of a pinch member and a supporting member.
FIG. 8 is a diagram showing a closed culture system.
FIG. 9 is a diagram showing closed culture systems including a flow-path selecting mechanism.
FIG. 10 is a diagram showing a reagent dispensing system of an automatic analysis device.
FIG. 11 is a diagram showing a reagent dispensing system including a flow-path selecting mechanism.

DESCRIPTION OF EMBODIMENTS

Embodiments are explained below with reference to the drawings.

FIG. 1 is an example in which eight tubes 1 are controlled by three universal-type pinch valves 2. The universal-type pinch valve is capable of performing two kinds of control of normal open and normal close with control of one actuator and has structure shown in FIG. 2. In the following explanation, when "pinch valve" is used without notice, the pinch valve indicates the universal-type pinch valve.

A pinch member 3 is fixed to a movable core 4 and moves according to a movement of the movable core 4. The pinch member 3 and the movable core 4 are collectively referred to as actuator as well. A supporting member 5 is fixed to a case 6. These members do not move. The supporting member 5 is configured from an NC (Normal Close)-side member 5a and an NO (Normal Open)-side member 5b. Tubes desired to be controlled are inserted between the supporting member 5 and the pinch member 3.

The actuator moves up and down in this figure with force by a spring 7 and magnetic force generated by a coil 8. When the coil 8 is not energized, the actuator is pushed up by the force of the spring 7 and the tube set on the NC side is crushed (pinched). When the coil 8 is energized, the actuator is attracted to a fixed core 9 side and the tube on the NO side is crushed. At this point, the tube on the NC side is restored by elasticity. Note that, as a driving source of the actuator, besides electromagnetism shown in the figure, pressure (air pressure or liquid pressure) or mechanical force of a cam or the like may be used.

The pinch member 3 and the supporting member 5 have shapes that enable a plurality of tubes to be simultaneously set respectively on the NC side and the NO side. It is possible to simultaneously control the set tubes.

A method of inserting eight tubs through pinch valves in three places is shown in FIG. 3. Eight tubes i to viii are inserted through pinch valves A, B, and C in three places in a state of (a). NC/NO states of the pinch valves are summarized for each of the tubes as shown in (b).

FIG. 4 shows a pinch-valve control method for tube selection. When the pinch valves in the three places are controlled in combinations of ON/OFF with respect to the tubes to be selected, the tubes can be brought into the open state.

(b) shows details of the control. (i) is a state in which all the pinch valves are OFF. At this point, the tube i is in the open state. When the pinch valve A is switched to ON, a state is as shown in (ii). The tube i is closed and the tube ii is brought into the open state. Similarly, any one of the eight tubes can be opened by controlling the pinch valves in the three places.

Eight kinds of control can be performed by the combinations of the three pinch valves. However, numbers of tubes may be used as explained below. For example, when it is attempted to select and control seven tubes, which is less than the eight tubes by one, with the three pinch valves, the respective tubes can be controlled. Even if the absent one tube is selected, the opening and closing of the remaining seven tubes are not affected. The number of tubes only has to be smaller than the number of combinations of the kinds of control of the pinch valves. $2^N$ kinds of control are possible with respect to the number N of the pinch valves. Therefore, N number of pinch valves only have to be present for selection of X number of flow paths satisfying $X \leq 2^N$.

If one tube is unused intentionally and is not used in the combinations in which the tube passes the NO side in all the pinch valves, when a power supply is turned off, a state can be obtained in which all the tubes are necessarily closed. It is possible to prevent the tubes from changing to the open state unexpectedly because of a power failure or the like. This serves as failsafe as well.

Note that, instead of the universal type, when an NC-type or NO-type pinch valve that switches one of open or close with one actuator is used, a function same as the function of the universal type can be realized by two combinations. Therefore, when 2N number of NC-type or NO-type pinch valves are prepared for selection of X number of flow paths satisfying $X \leq 2^N$, the flow path selection explained above is also possible.

First Embodiment

In an embodiment explained below, a method of setting tubes in pinch valves is explained.

In the flow-path (tube) selecting method of the present invention, a method of inserting a plurality of tubes through pinch valves is important. However, on the other hand, the method is complicated. Therefore, if it is attempted to set the tubes one by one, it takes time. Likelihood of erroneous insertion cannot be eliminated. Therefore, it is desirable that tubes to be on an NC side and tubes to be on an NO side in the pinch valves are sorted and collected in advance and can be collectively set.

An example of the setting is shown in FIG. 5. A tube holder 10 includes two tube holding sections 10a and 10b, which respectively hold the tubes for NC and for NO. The tube holder 10 includes a fitting section 10c such that the tube holder 10 can be slid and fit in the supporting member 5 of the pinch valve. The tubes 1 are sorted for NC and for NO and inserted through the tube holder 10 in advance. By fitting the tube holder 10 in the supporting member 5 of the pinch valve, the tubes 1 are set in the pinch valve. A tube set may be prepared in which $2^N$ number of tubes 1 are inserted through N number of tube holders 10 in a correct combination in advance. A user is released from a trouble of inserting the tubes.

To prevent the NC side and the NO side from being mistaken when the tube holder is fit in the supporting member, there may be an idea for forming the shape of the fitting section asymmetrical to provide a mechanism for wrong fitting prevention. When there are a plurality of tube holders and a plurality of pinch valves, there may be an idea for coloring supporting members for the tube holders and the pinch valves forming pairs to distinguish the supporting members.

Since it is important to sort the tubes in advance, the tubes may be divided into the NC side and the NO side and the tubes on the NC side and the tubes on the NO side may be respectively bound by a tape or an adhesive rather than being held by the tube holder 10.

The NC side of the pinch valve is narrow and it is hard to insert the tubes through the NC side. Therefore, the tubes may be inserted through the NO side and the NC side in order while switching the position of the pinch member 3. The tube holder 11 shown in FIG. 6 includes two tube holding sections 11a and 11b and a flexible portion 11c. It is desirable to insert the tube on the NO side first, subsequently drive the actuator to open the NC side, and insert the tube on the NC side. There may be an idea for preventing erroneous insertion on the NC side and the NO side. For example, the tubes may have a shape for disabling the erroneous insertion or there may be an idea for coloring the tubes to make the erroneous insertion less easily occur.

The pinch member and the supporting member may be detachable from the pinch valve. A tube set may be prepared in a state in which the pinch member and the supporting member are incorporated in the tubes. As shown in FIG. 7(a), a pinch valve 12 can be disassembled into a main body 12a, a pinch member 12b, and a supporting member 12c. The supporting member 12c can be further disassembled into 12c1 and 12c2. As shown in (b), the tube for NO is inserted between the supporting member 12c2 and the pinch member 12b, the tube for NC is inserted over the tube for NO, and the supporting members 12c1 and 12c2 are combined. In such a state, the tubes may be prepared as the tube set. If a snap-fit structure is adopted as a method for the combination, inexpensive and easy combination is possible. When the pinch valve 12 is used, as shown in (c), the supporting member 12c2 and the pinch valve main body 12a are combined and the pinch member 12b and the actuator 12d are combined. Note that, in the combination of the pinch member 12b and the actuator 12d, up-down movements of the actuator have be able to be transmitted to the pinch member. For example, a snap-fit is desirably adopted in which a projecting section is fit in a recessed section and a positional relation between the projecting section and the recessed section is restrained.

Note that the flow path treated in the present invention is not limited to a circular tube structure. Besides the tube, the present invention can also be applied to, for example, a flow path formed by sticking together films. The flow path only has to be a flow path deformable with respect to a pinch force of the pinch valve and having elasticity or flexibility.

Second Embodiment

An embodiment explained below is an example in which the flow-path control method is applied to a cell culture device.

Among cell culture devices, there is a cell culture device that connects a supply bag or a collection bag, in which a culture medium is stored, to a closed culture vessel including a lead-in port and a discharge port for fluid to form one closed system (hereinafter, closed culture system) and performs culture medium exchange on the inside of the system to cultivate a cell. A method of the cell culture device is described in, for example, Patent Literature 2 described above. Since the system is the closed system, there is an advantage that there is no risk of contamination from the outside. However, there is a limitation that control of liquid has to be basically performed from the outside of the system. The pinch valve can be controlled from the outside of the system. Therefore, the pinch valve is a control member suitable for this device.

The closed culture system is shown in FIG. 8. A supply bag 14 and a collection bag 15 are connected to a culture vessel 13, which includes an inlet and an outlet, via tubes (an upstream side 16 and a downstream side 17). The culture vessel 13 is in a closed state. A driving force for liquid needs to be applied from the outer side. The tube is squeezed from the outer side by a squeezing pump 18 to feed the liquid. Note that the squeeze pump 18 may be set in any one of the tubes on the upstream side and the downstream side.

When singularities of the culture vessel, the supply bag, and the collection bag are present and a branch is absent, as shown in FIG. 8, it is unnecessary to control a flow path. However, when pluralities of the culture vessels, the supply bags, and the collection bags are present and connected in parallel, the liquid has to be fed while selecting a flow path. The flow-path selection method of the present invention is applied to the selection of the flow path.

An example in which the supply bags are connected in parallel is shown in FIG. 9(a). As liquid types necessary for cell culture, there are a cell suspension, a culture medium, cleaning liquid, oxygen liquid, and the like. The cell culture device desirably can simultaneously treat a plurality of supply bags. A plurality of supply bags 14 are respectively connected to a common flow path 16 by individual flow paths 19. A flow-path selecting mechanism 20 is placed in a place where the individual flow paths 19 are arranged side by side. The flow-path selecting mechanism 20 is a mechanism including N number of universal-type pinch valves and is a mechanism capable of selecting $2^N$ number of flow paths. The flow-path selecting mechanism 20 controls the flow paths such that any one of the flow paths is opened.

A peristaltic pump 18 is set in an upstream or downstream common flow path portion. After the flow path is selected, by driving the peristaltic pump, a selected liquid type is sent to the culture vessel.

FIG. 9(b) is an example in which a plurality of culture vessels are present and connected in parallel. Culture vessels are often increased to increase a yield. A plurality of cells are cultivated to serve for an inspection separately from cells for transplanting. A plurality of culture vessels 13 are placed in parallel and respectively connected to a common flow path by individual flow paths 21. If the flow-path selecting mechanism 20 is placed in a place where the individual flow paths 21 are arranged side by side, it is possible to select a culture vessel to which liquid is sent. The flow-path selecting mechanism 20 may be set on an upstream side of the culture vessel or may be set on a downstream side of the culture vessel.

FIG. 9(c) is an example in which a plurality of collection bags are present and connected in parallel. When it is desired to separate a collected object, such a connection method can be used. If a common flow path 17 branches to individual flow paths 22 and the flow-path selecting mechanism 20 is set in a place where the common flow path 17 branches, it is possible to select a collection destination.

The connection methods explained above may be combined as shown in FIG. 9(d). For example, pluralities of supply bags 14, culture vessels 13, and collection bags 15 are present and connected via upper and lower common paths 16 and 17. If the flow-path selecting mechanisms 20 are set in places of respective individual flow paths, it is possible to feed any liquid type to any culture vessel and collect the liquid type in any collection destination.

As shown in FIG. 9(e), M number of supply bags and N number of culture vessels are connected in M×N combinations. Although flow paths are complicated, since the flow paths are not shared, there is an advantage that carryovers of different liquid types do not occur upstream. M number of supply bags 14 and N number of culture vessels 13 are connected to each other by (M×N) number of individual flow paths 23. The flow-path selecting mechanism 20 only has to be set in a place of the individual flow paths 23. Note that, even if the number of flow paths is large on the upstream side, if the flow paths are collected as one flow path on the downstream side, only one driving source (squeezing pump) has to be provided.

When it is desired to separate a plurality of collected objects from the culture vessel, if carryovers should not be present in the collected objects at all, the collected objects may be divided on the collection side as shown in (f). P number of culture vessels 13 and Q number of collection bags 15 are connected to each other by (P×Q) number of individual flow paths 24. The flow-path selecting mechanism 20 only has to be set in a place of the individual flow paths 24. If the flow paths on the upstream side are collected as one flow path, only one driving source has to be provided.

Third Embodiment

An embodiment explained below is an example in which the flow-path control method is applied to an automatic analysis device.

In the automatic analysis device, there is, for example, a reagent dispensing system shown in FIG. 10. A flow path 32 leading to a reagent container 31 is connected to one side of a three-way switching valve 30. A flow path 34 leading to a nozzle 33 is connected to the other side of the three-way switching valve 30. A common port of the three-way switching valve 30 is connected to a syringe 36 via a flow path 35. When the three-way switching valve 30 is directed to the reagent container 31 side and the syringe 36 is pulled, it is possible to suck a reagent to the syringe side. When the three-way switching valve 30 is switched to the nozzle 33 side and the syringe 36 is pushed, it is possible to discharge the reagent from the nozzle.

To treat a plurality of reagent, the automatic analysis device only has to include a plurality of the reagent dispensing systems. However, as a method of controlling the reagents with one syringe, there is a method of controlling the reagents using a multiple switching valve. The method is described in, for example, Patent Literature 1 described above. Flow paths of a plurality of reagent dispensing systems are connected to one side of the multiple switching valve, a syringe is connected to the other side of the multiple switching valve, and the reagent dispensing system is selected to control the syringe. Consequently, it is possible to dispense any reagent.

In the multiple switching valve described in Patent Literature 1, slide valves are pressed against each other to be switched. Therefore, the slide valves are switched without a leak. However, because of the pressing structure, a leak from the pressed portion is not zero. In order to reduce the leak as much as possible, maintenance is extremely important and time-consuming.

As shown in FIG. 11, the flow paths 35 extending from common ports of three-way switching valves of a plurality of reagent dispensing systems are collected as a common flow path 37. A common syringe 38 is connected to the common flow path 37. The flow-path selecting mechanism 20 of the present invention is set in a place of the plurality of individual flow paths 35. By operating the syringe 38 after selecting a flow path with the flow-path selecting mechanism 20, it is possible to dispense any reagent. With this method, since the reagent dispensing systems remain as close systems, a leak could not occur. There is an advantage that maintenance is easy.

REFERENCE SIGNS LIST 1 tube
2 pinch valve
3 pinch member
4 movable core
5 supporting member
6 case
7 spring
8 coil
9 fixed core
10 tube holder
11 tube holder
12 pinch valve
13 culture vessel
14 supply bag
15 collection bag
16 upstream side tube
17 downstream side tube
18 squeezing pump
19 individual flow path
20 flow-path selecting mechanism
21 individual flow path
22 individual flow path
23 individual flow path
24 individual flow path
30 three-way switching valve
31 reagent container
32 flow path
33 nozzle
34 flow path
35 flow path
36 syringe
37 common flow path
38 syringe

The invention claimed is:

1. A flow-path control device comprising:
X number (X≥3) of flow paths; and
a minimum N number of valves satisfying $X \leq 2^N$;
wherein each of the valves includes a housing, a moveable member, an actuator that is connected to drive a moveable member, a first fixed member that is fixed to the housing and has a portion extending parallel to the moveable member on a first side of the moveable member and a second fixed member that is fixed to the housing and has a portion extending parallel to the moveable member on a second side of the moveable member, wherein, for each of the valves, the first fixed member, the second fixed member, and a portion of the moveable member that is parallel to the first fixed member and the second fixed member traverse the flow paths, wherein each of the valves is disposed in a different position along a flow direction of the flow paths, wherein a first plurality of the X number of flow paths pass on the first side of the moveable member between the moveable member and the first fixed member, and a second plurality of the X number of flow paths pass on the second side of the moveable member between the moveable member and the second fixed member, wherein each of the X number of flow paths pass the respective moveable member of each valve, and wherein the flow-path control device opens any one of the X number of flow paths by simultaneously controlling each of the N number of valves.

2. The flow-path control device according to claim 1, wherein, for each of the valves, respective portions of the first fixed member, the second fixed member, and the portion of the moveable member that is parallel to the first fixed member and the second fixed member perpendicularly traverse the flow paths.

3. A cell culture device using the flow-path control device according to claim 1, in which a supply bag for storing liquids necessary for culture and a collection bag for collecting liquid after use are connected to a culture vessel of a closed system including a lead-in port and a discharge port for fluid, the cell culture device forming a closed system and performing culture of a cell in the closed system, wherein X number of the supply bags are present, and the supply bags are connected to one common flow path in parallel via the flow-path control device.

4. The cell culture device using the flow-path control device according to claim 3, wherein a liquid driving source is provided in a common flow path section.

5. A cell culture device using the flow-path control device according to claim 1, in which a supply bag for storing liquids necessary for culture and a collection bag for collecting liquid after use are connected to a culture vessel of a closed system including a lead-in port and a discharge port for fluid, the cell culture device forming a closed system and performing culture of a cell in the closed system, wherein X number of the culture vessels are present, and the culture vessels are connected to respective common flow paths on one of the lead-in port side or the discharge port side in parallel via the flow-path control device.

6. The cell culture device using the flow-path control device according to claim 5, wherein a liquid driving source is provided in a common flow path section.

7. A cell culture device using the flow-path control device according to claim 1, in which a supply bag for storing liquids necessary for culture and a collection bag for collecting liquid after use are connected to a culture vessel of a closed system including a lead-in port and a discharge port for fluid, the cell culture device forming a closed system and performing culture of a cell in the closed system, wherein X number of the collection bags are present, and the collection bags are connected to one flow path in parallel via the flow-path control device.

8. The cell culture device using the flow-path control device according to claim 7, wherein a liquid driving source is provided in a common flow path section.

9. A cell culture device using the flow-path control device according to claim 1, in which a supply bag for storing liquids necessary for culture and a collection bag for collecting liquid after use are connected to a culture vessel of a closed system including a lead-in port and a discharge port for fluid, the cell culture device forming a closed system and performing culture of a cell in the closed system, wherein X number of the supply bags and X number of the culture vessels are respectively present, and the supply bags and the culture vessels are connected by the X number of flow paths.

10. A cell culture device using the flow-path control device according to claim 1, in which a supply bag for storing liquids necessary for culture and a collection bag for collecting liquid after use are connected to a culture vessel of a closed system including a lead-in port and a discharge port for fluid, the cell culture device forming a closed system and performing culture of a cell in the closed system, wherein X number of the culture vessels and X number of the collection bags are respectively present, and the culture vessels and the collection bags are connected by the X number of flow paths.

11. A cell culture device using the flow-path control device according to claim 2, in which a supply bag for storing liquids necessary for culture and a collection bag for collecting liquid after use are connected to a culture vessel of a closed system including a lead-in port and a discharge port for fluid, the cell culture device forming a closed system and performing culture of a cell in the closed system, wherein X number of the supply bags are present, and the supply bags are connected to one common flow path in parallel via the flow-path control device.

12. A cell culture device using the flow-path control device according to claim 2, in which a supply bag for storing liquids necessary for culture and a collection bag for collecting liquid after use are connected to a culture vessel of a closed system including a lead-in port and a discharge port for fluid, the cell culture device forming a closed system and performing culture of a cell in the closed system, wherein X number of the culture vessels are present, and the culture vessels are connected to respective common flow paths on one of the lead-in port side or the discharge port side in parallel via the flow-path control device.

13. A cell culture device using the flow-path control device according to claim 2, in which a supply bag for storing liquids necessary for culture and a collection bag for collecting liquid after use are connected to a culture vessel of a closed system including a lead-in port and a discharge port for fluid, the cell culture device forming a closed system and performing culture of a cell in the closed system, wherein X number of the collection bags are present, and the collection bags are connected to one flow path in parallel via the flow-path control device.

14. A cell culture device using the flow-path control device according to claim 2, in which a supply bag for storing liquids necessary for culture and a collection bag for collecting liquid after use are connected to a culture vessel of a closed system including a lead-in port and a discharge port for fluid, the cell culture device forming a closed system and performing culture of a cell in the closed system, wherein X number of the supply bags and X number of the culture vessels are respectively present, and the supply bags and the culture vessels are connected by the X number of flow paths.

15. A cell culture device using the flow-path control device according to claim 2, in which a supply bag for storing liquids necessary for culture and a collection bag for collecting liquid after use are connected to a culture vessel of a closed system including a lead-in port and a discharge port for fluid, the cell culture device forming a closed system and performing culture of a cell in the closed system, wherein X number of the culture vessels and X number of the collection bags are respectively present, and the culture vessels and the collection bags are connected by the X number of flow paths.

\* \* \* \* \*